(12) United States Patent
Axelrod et al.

(10) Patent No.: US 8,476,005 B2
(45) Date of Patent: *Jul. 2, 2013

(54) MICROFLUIDIC EMBEDDED POLYMER NEMS FORCE SENSORS

(75) Inventors: Blake W. Axelrod, Pasadena, CA (US); Michael L. Roukes, Pasadena, CA (US); Jessica L. Arlett, South Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 964 days.

This patent is subject to a terminal disclaimer.

(21) Appl. No.: 12/364,666

(22) Filed: Feb. 3, 2009

(65) Prior Publication Data

US 2010/0041091 A1    Feb. 18, 2010

Related U.S. Application Data

(60) Provisional application No. 61/063,603, filed on Feb. 5, 2008.

(51) Int. Cl.
*C12Q 1/02*   (2006.01)
*C12P 1/00*   (2006.01)
*C12M 3/00*   (2006.01)
*C12N 1/38*   (2006.01)

(52) U.S. Cl.
USPC .............. 435/4; 435/29; 435/41; 435/287.1; 435/288.5; 977/724; 977/732

(58) Field of Classification Search
None
See application file for complete search history.

(56) References Cited

U.S. PATENT DOCUMENTS

| 7,353,705 | B2 * | 4/2008 | Mori et al. ................. 73/504.12 |
| 2002/0166962 | A1 * | 11/2002 | Roukes et al. ................ 250/306 |
| 2003/0062193 | A1 * | 4/2003 | Thaysen et al. ............... 174/255 |
| 2005/0103996 | A1 * | 5/2005 | Olin et al. ..................... 250/311 |
| 2005/0161749 | A1 * | 7/2005 | Yang et al. .................... 257/414 |
| 2006/0075803 | A1 * | 4/2006 | Boisen et al. ................ 73/31.06 |
| 2007/0266797 | A1 * | 11/2007 | Hirabayashi et al. .... 73/862.044 |
| 2010/0024572 | A1 * | 2/2010 | Roukes et al. ........... 73/862.625 |

OTHER PUBLICATIONS

Wakatsuki, T et al. Phenotypic screening for pharmaceuticals using tissue constructs. Current Pharmaceutical Biotechnology 2004 vol. 5 pp. 181-189.*
Woo, Jean. Age related changes in protein binding of drugs: implications for therapy. Journal of the Hong Kong Geriatrics Socieity. 1999 vol. 9 No. 1 pp. 14-17.*
Rotsch et al. Biophysical Journal 2000 vol. 78 pp. 520-535.*
Ko et al. Journal of Cell Science 2001 vol. 114 pp. 1155-1167.*
BASF, Pluronic® F127 Block Copolymer Surfactant, in Technical Bulletin. 2002 Mount Olive, 1 page.
Canaria et al., "Formation and removal of alkylthiolate self-assembled monolayers on gold in aqueous solutions," Lab on a Chip, 2006 6(2): 289-295.

(Continued)

*Primary Examiner* — Betty Forman
(74) *Attorney, Agent, or Firm* — Foley & Lardner LLP (57) ABSTRACT

A method of screening one or more cells is described; the method includes: (i) providing one or more cells to a nanoelectromechanical system (NEMS) force sensor; (ii) applying at least one reagent to the one or more cells; and (iii) observing a response of the one or more cells to the reagent with the force sensor, thereby screening the one or more cells.

22 Claims, 3 Drawing Sheets

OTHER PUBLICATIONS

Chrzanowska-Wodnicka et al., "Rho-stimulated contractility drives the formation of stress fibers and focal adhesions," J. Cell. Biol., Jun. 1, 1996, 133:1403-1415.

Cramer et al., "Role of actin-filament disassembly in lamellipodium protrusion in motile cells revealed using the drug jasplakinolide," Current Biology, Sep. 23, 1999, 9:1095-1105.

Foissner et al., "Wide-ranging effects of eight cytochalasins and Latrunculin A and B on intracellular motility and actin filament reorganization in characean internodal cells," Plant Cell Physiol., 2007, 48(4):585-597.

Geerken et al., "Chemical and thermal stability of alkylsilane based coatings for membrane emulsification," Advanced Engineering Materials, 2004. 6(9):749-754.

Hong, Jongin, "Microfluidic Systems for High Throughput Screening," Biochip Journal, Mar. 2008, 2(1):12-26.

Ishiguro et al., "Isolation and characterization of mutants supersensitive to the spindle position, Isopropyl N-3-chlorophenyl carbamate (CIPC) in the fission yeast Schizosaccharomyces pombe," Jpn. J. Genet., 1992, 67:97-109.

Itoh et al., "An essential part for Rho-associated kinase in the transcellular invasion of tumor cells," Nature Medicine, Feb. 1999, 5(2):221-225.

Janmey, Paul A., "The Cytoskeleton and Cell Signaling: Component Localization and Mechanical Coupling," Physiological Reviews, 1998, 78(3): 763-781.

Jordan et al., "Microtubules as a target for anticancer drugs," Nature Reviews Cancer, Apr. 2004, 4:253-265.

Kempiak et al., "A neural Wiskott-Aldrich syndrome protein-mediated pathway for localized activation of actin polymerization that is regulated ty Cortactin," J. Biol. Chem., Feb. 18, 2005, 280(7):5836-5842.

Korn et al., "Cell-based high-content screening of small-molecule libraries," Current Opinion in Chemical Biology, 2007, 11:503-510.

Kovacs et al., "Mechanism of Blebbistatin Inhibition of Myosin II," J. Biol. Chem., Aug. 20, 2004, 279(34):35557-35563.

Melin et al., "Microfluidic Large-Scale Integration: The Evolution of Design Rules for Biological Automation," Annual Review of Biophysics and Biomolecular Structure, 2007, 36:213-231.

Myszka et al., "Kinetic analysis of a protein antigen-antibody interaction limited by mass transport on an optical biosensor," Biophys. Chem., 1997, 64:127-137.

Newman, J., The fundamental principles of current distribution and mass transport in electrochemical cells. in Electroanalytical Chemistry, vol. 6 (ed. Bard, A.) 279-297, (Dekker, New York, 1973).

Squires et al., "Making it stick: convection, reaction and diffusion in surface-based biosensors," Nature Biotechnology, 2008, 26(4):417-426.

Stull et al., "Vascular Smooth Muscle Contractile Elements," Hypertension, Jun. 1991, 17(6, Part 1):723-732.

Tan et al., "A simple approach to micropattern cells on common culture substrates by tuning substrate wettability," Tissue Engineering, 2004, 10(5-6): 865-872.

Wakatsuki et al., "Phenotypic screening for pharmaceuticals using tissue constructs," Current Pharmaceutical Biotechnology, 2004, 5:181-189.

Watanabe et al., "Cooperation between mDia1 and ROCK in Rho-induced actin reorganization," Nature Cell Biology, 1999, 1(3):136-143.

Wen et al., "The future of microfluidic assays in drug development," Expert Opin. Drug Discov., 2008, 3(10):1237-1253.

* cited by examiner

MICROFLUIDIC EMBEDDED POLYMER NEMS FORCE SENSORS

RELATED PATENT APPLICATIONS

This application claims priority to U.S. Provisional Application Ser. No. 61/063,603, filed Feb. 5, 2008, which is incorporated herein by reference in their entirety.

FEDERAL FUNDING STATEMENT

This invention was made with government support under grant number ARO W911NF-04-1-071 awarded by the Army Research Office. The Government has certain rights in the invention.

BACKGROUND OF THE INVENTION

The development of microcantilever force sensors has enabled development of instrumentation such as atomic force microscope (AFM) tools, which have further led to the development of cantilever based sensing. However, at microscale dimensions, there are limits with respect to the level of frequency achievable and the level of sensitivity attainable. In this regard, the standard approaches used to make microelectromechanical systems (MEMS) provide little access to the nanoscale, where large improvement in sensitivity can be attained.

Cells exert forces on their surroundings using their cytoskeleton. The cytoskeleton is a very complex and dynamic structure which is directly coupled to all organelles within a cell and many, if not all, signaling networks within a cell (Janmey, P. A., *Physiological Reviews* 87 (1998) 763-781). Thus, monitoring the state of a cell's cytoskeleton is a promising approach for performing phenotypic screening of potential pharmaceutical reagents for both desired and undesired activity within a cell.

The ability to measure forces exerted by biological specimen have encountered significant limitations. To overcome this limitation, prior work has been focusing on optical measurement techniques. However, such technique is often limited by the resolution attainable. Additionally, some prior efforts of delivery and control systems fail to maintain the viability of the biological sample under study, while providing a mechanism to extract signals from a force sensor to a computer for readout and analysis.

Tissue constructs have been used to perform phenotypic screening of pharmaceutical by monitoring the contraction of large populations of cells. However, results from tissue construct often are low in resolution, and thus subtle effects may be missed. Another drawback of tissue constructs is that they are slow to form and grow. Tissue constructs can also demand relatively large quantities of reagents and are not amenable to large scale integration/automation nor to simultaneous fluorescent microscopy.

Thus, a need exists for an improved force sensor system to provide better monitoring and measuring techniques of biological cells.

BRIEF SUMMARY OF THE INVENTION

Nanoelectromechanical system (NEMS) force sensors, when applied to biological applications, can measure the force exerted by a single cell on its surroundings with unparalleled sensitivity.

A method of screening one or more cells is described, the method comprising: (i) providing one or more cells to a nanoelectromechanical system (NEMS) force sensor; (ii) applying at least one reagent to the one or more cells; and (iii) observing a response of the one or more cells to the reagent with the force sensor, thereby screening the one or more cells.

A method of evaluating effects of a drug reagent, comprising: (i) providing one or more cells to a nanoelectromechanical system (NEMS) force sensor; (ii) applying the drug reagent to the one or more cells; and (iii) observing a response of the one or more cells to the drug reagent with the force sensor, whereby an effect of the drug reagent on the one or more cells is evaluated.

BRIEF DESCRIPTIONS OF THE FIGURES

FIGS. 1a-1b show images and schematic illustrating how a cell deforms a force sensing beam upon contraction.

FIGS. 2a-2i illustrate NEMS-enabled single-cell force measurements with high temporal and force resolution. FIGS. 2a-2b provide optical images showing a microfluidics encapsulated force sensor, and FIG. 2c provides an electron micrograph thereof. FIG. 2d shows an NIH-3T3 cell attached to a microfluidics encapsulated force sensor in a microscope-mounted incubator and sample holder. FIG. 2e shows force versus time data from a contracting and relaxing lamellipodium, as the cell is perturbed with cytochalasin D and allowed to recover in growth media (as shown in FIG. 2b). The force data was acquired with a force resolution of 200 pN and a time resolution of 100 ms—25× and 300×, respectively, better than prior state of the art. FIGS. 2f-2h provide plots that show force signatures of two molecular-mechanical processes: small force oscillations, roughly 400 pN peak-to-peak, with a frequency that is monotonically dependent on the force being exerted by the lamellipodium shown in FIG. 2f, with FIG. 2g illustrating the linearity of frequency dependence. FIGS. 2h-2i show that large, stable, quantized force steps of order 1 nN are manifested when a cell's cytoskeleton is perturbed with cytochalasin D and allowed to recover in growth media. A histogram of the step sizes is presented in FIG. 2j.

FIGS. 3a-3d show results from surface chemistry Petri dish experiments.

DETAILED DESCRIPTIONS OF THE INVENTION

All references cited herein are incorporated by reference in their entirety.

Device Fabrication

The NEMS devices can be fabricated from lithographically patternable polymer instead of traditional MEMS materials, such as silicon, because polymer's low Young's modulus can enable improved sensitivity and fabrication of devices that are compliance-matched to typical biological materials. Additionally, the material costs for polymers can be significantly less than traditional semiconductor materials. This can be significant, particularly when, for example, the force sensor system described herein comprises an array of sensors.

In one embodiment, a long-trench-shaped cell chamber, which is spanned by the force sensing beams (or "force sensor") and a bridge to hold the cell being studied in close proximity to the beams can be made. The chamber can have any suitable size. For example, in one embodiment it can be roughly 600-800 microns long and 110 microns wide, or it can be longer or shorter, wider or narrower, depending on the use. The cantilevers (or "beams") of the force sensor can be fabricated from two layers of polymer that can sandwich a strain sensor (or "strain gauge"), thus keeping the strain sensor from the surrounding liquid and symmetric—decoupled—with respect to out-of-plane deflections. The liquid can come from a microfluidics channel that can be embedded and integrated with the system. The microfluidics can, for example, encapsulate the force sensor. The polymer layer can be, for example, between 50 nm and 200 nm thick, such as about 80 nm to about 150 nm thick, such as about 100 nm thick.

The strain sensor can comprise at least a metal wire. The metal wire can comprise any suitable metal, such as a noble metal, including gold. The wire can be a part of a transducer, such as a piezoresistive or piezoelectric device, such as a piezoresistor (PZR). Two additional metal layers can be involved: the "pad" layer which can sit on the top surface of the force sensing beams and the cell bridge to define a region where the cell will attach and the "conductor" layer which can be a thick layer of metal that connects the PZR stain gauge out to contact pads that can be contacted with pogo-pins, thermal bonded flex circuits, wire bonds or any other suitable microchip circuit bonding technique. The area on the force sensor to be in contact with the cells an be defined by, for example, a metal region or grid of metal regions. Such regions or grids can be where a biological sample, such as a cell, exerts force on the sensor.

The chip can contain multiple cell chambers, such as four cell chambers, with, for example, one cell bridge and two force sensors per chamber, for a total of eight force sensors per chip. In one embodiment, there can be forty electrical connections for contacting the eight force sensors on each chip. Additional room can added for the microfluidics. In one embodiment, the resulting chips can be about 18 mm×18 mm.

The polymers of the force sensors can comprise and/or be fabricated from different types of polymers. For example, the polymers can comprise an epoxy-based photoresist, such as SU-8, including SU-8-3000 series polymers, polyimide, poly-para-xylene polymer, such as parylene, or combinations thereof. The polymer can be cured or uncured, depending on the application. In one embodiment, the SU-8 polymer that is used in the sensor is cured and baked. The force sensor can be recyclable or can be disposable.

In one embodiment, a microfluidics embedded NEMS force sensor can be fabricated by first depositing a polymer layer onto a silicon nitride membrane layer. The membrane layer can be disposed over a silicon wafer. A metal wire, or a strain sensor, comprising a piezoresistive element can be deposited onto the polymer layer. An additional polymer layer can then be deposited onto the metal wire. The polymer layers need not comprise the same material, but can, if suitable. The polymer, as described previously, can comprise any polymer, including parylene, SU-8, polyimide, or combinations thereof. The backside of the wafer can be etched to create a hole. As a result of this process, in this embodiment, a NEMS force sensor can be fabricated from two layers of polymer, encapsulating a metal wire. The force sensor is suspended over a hole, with a portion of the silicon-nitride membrane removed without damage to the polymer layers.

Silicon Nitride Process

The use of silicon nitride membrane in MEMS device fabrication and/or application is generally known. The polymer-based NEMS device in one embodiment can be fabricated on top of a nitride membrane, which membrane can then be removed from beneath the NEMS device, allowing the devices to be suspended at least partially over an opening etched in the underlying layer. The opening can be etched through the backside of the underlying layer. In one alternative embodiment, the polymer NEMS devices can be fabricated on a silicon substrate and suspended using a through wafer etch, with the nitride membrane acting only as an etch stop for the through wafer etch.

A wafer, such as a silicon wafer, can be used as a substrate on which a force sensor is fabricated. Silicon wafers are compatible with micro and nano fabrication techniques and are generally suitable for use with micro and nano fabrication techniques. The silicon wafer can be further coated with a material to create a membrane. The material can be any suitable material, including silicon nitride, silicon dioxide, or a combination thereof. In one embodiment, the membrane can serve as an etch stop for the thru-wafer etch. The thru-wafer etch can be performed with, for example, potassium hydroxide (KOH), tetra-methyl ammonia hydroxide (TMAH), a plasma etch (e.g., a deep-RIE), or a combination thereof. Silicon nitride can be particularly suitable as the material for the membrane because the internal stress of the nitride can be well-controlled during the nitride deposition—an internal stress of 100-200 MPa can be desirable for membrane fabrication. Additionally, silicon nitride is a hard and strong material, and it has relatively high resistance to KOH and TMAH.

One important step in the nitride process can be developing an etch that would remove the silicon nitride membrane from below the polymer beams without damaging the beams. The silicon-nitride membrane can first be deposited on a wafer, such as a silicon wafer. In one embodiment, the nitride membrane can be defined by opening a window in the nitride layer, using, for example, lithography and an etch, such as a fluorine plasma, on the back of the wafer and subsequently etching thru the silicon portion of the wafer, using, for example, KOH, TMAH, deep-RIE or a combination thereof, until substantially all of the silicon is removed beneath the nitride on the front of the wafer, thus suspending that nitride and creating the membrane. The opening can be a part of the microfluidics channel, for example, which channel can be surrounding the force sensor. In one embodiment, after the membrane has been defined beneath the polymer devices using backside alignment and a potassium hydroxide (KOH) etch through the wafer, a $CF_4$—$O_2$ plasma can be used to etch almost all of the way through the nitride membrane. The $CF_4$—$O_2$ plasma, or any plasma etch for that matter, can etch through the polymer beams much faster than through the silicon nitride, or any crystalline material. The final layer of nitride, can be removed using a heated 0.1% hydrofluoric acid etch at 80° C., which can be used in combination of a fluorine based plasma. In general, hydrofluoric acid does not etch polymers, and when dilute and heated, can preferentially etch silicon nitride over silicon dioxide. Such fabrication process can allow for a large yield of NEMS devices. For example, in one embodiment, the yield can be greater than 60%, such as greater than 70%, such as greater than 80%.

Microfluidics

A microfluidics channel can be integrated with the force sensor system. For example, it can encapsulates the force sensor, wherein the microfluidics channel can control the fluidic environment around the force sensor. One advantage of such design is that the microfluidics can improve the electrical read out of the electrical signal from the sensor.

Microfluidics can involve any suitable materials, such as polymer. For example, it can comprise a polymer, such as parylene, polyimide, or a siloxane polymer. Descriptions of a Polydimethyl-siloxane (PDMS) microfluidics process can be found in, for example, Melin et al., *Annual Review of Biophysics and Biomolecular Structure* 36 (2007), 213-231. PDMS is a FDA approved food handling material and is a two part silicone based elastomer: a base and a curing agent whose components can undergo a hydrosilylation reaction upon cross-linking. The base comprises dimethylsiloxane oligamers with vinyl-terminated end groups, platinum catalyst, and silica filler. The curing agent comprises a cross-linking agent (dimethylmethylhydrogen siloxane) and an inhibitor (tetramethyl tetravinyl cyclotetrasiloxane). When the two parts are mixed, cross-linking can occur when the vinyl and silicon hydride groups undergo a hydrosilylation reaction to form a Si—C bond. The cross-linking reaction can occur at room temperature but can be accelerated by heating to, for example 80° C., which is compatible with polystyrene Petri dishes. PDMS can be coated over a substrate, such as a glass coverslip.

The microfluidics channels and valves can be fabricated by molding multiple layers of PDMS over photo lithographically fabricated molds. For example, alternating layers of PDMS can be fabricated having either excess curing agent or excess base agent, partially curing each piece, bringing the two pieces together and then curing the complete assembly. This ability to stack and cure together layers of PDMS can enable complex microfluidics. PDMS can be permeable to gas, particularly to oxygen, nitrogen, and carbon dioxide. This property can be desirable for removing air bubbles from fluid channels and for keeping cells alive with fresh oxygen within the PDMS channels.

The microfluidics can be important for confining the available acoustic modes within the fluid chamber to high frequencies that do not interfere with a measurement process. The microfluidics can also be important for delivering cells directly to the force sensors. In one embodiment, microfluidics can be enable precise pharmacological perturbation of the cell when it is on the force sensor. For example, the media flow past the cell can be controlled with the microfluidics. The microfluidics can be computer controlled, such as through an Igor graphical user interface (GUI). In addition to basic valve actuation, the GUI can include a user friendly interface for easily creating custom sequences and fluidic programs for automating surface chemistry protocols, tissue culture protocols, cleaning protocols. This ability can be useful for standardizing both tissue culture and cell perturbation protocols, as well as optimizing time to increase throughput (e.g. cleaning and surface chemistry protocols can be run unattended at night).

Force Sensor

The NEMS force sensor can comprise deformable polymer layers and metal layers, as described previously. For example, it can comprise a deformable member that can be integrated with a strain sensor. The strain sensor can be used to convert the deformation of the deformable member, resulting from the response of the cells, such as force exerted by the cells, into an electrical signal. The force sensor can further comprise a microfluidics channel that can encapsulate the force sensor, wherein the microfluidics channel can control a fluidic environment around the force sensor. The microfluidics can also improve the readout of the electrical signals from the force sensor.

The deformable member can comprise a doubly clamped beam. For example, it can comprising two polymer layers sandwiching a metal wire. The metal wire can be, for example, a gold wire. The gold wire can be part of the strain sensor, which can be piezoresistive or piezoelectric. The strain sensor can also comprise a transducer. In one embodiment, the wire can be a part of the transducer, which can be sandwiched between two polymer layers. The strain sensor can be patterned asymmetrically through the doubly clamped beam to measure in-plane signals, such as force and/or tensile or compressive strain exerted or caused by the cells in the in-plane direction. The asymmetry can be in the form of a zig-zag pattern in a horizontal plane of the beam. The strain sensor can also have a variety of shape. For example, it can have a c-shape. The asymmetry can allow the sensor to detect the in-plane signals with high resolution. In the out-of-plane direction, the strain sensor can be patterned symmetrically though the doubly clamped beam. Alternatively, the strain sensor comprises a piezoresistive strain sensor that is patterned asymmetrically in a vertical plane of the doubly clamped beam to measure out-of-plane responses. As described previously, additional metal layers can be deposited. For example, a metal layer for controlling cell adhesion to the force sensor can be deposited. Such layer, for example, can be adhered to the wafer substrate with an organic adhesion promoter and patterned using metal liftoff.

The force sensor can also have shapes different from a beam or cantilever. For example, it can have a shape of a plate, such as a square plate. In on embodiment wherein the sensor has a shape of a square plate, the sensor can be adapt for detecting vibration signals, such as oscillation, affected by the cells. The sensitivity of square plate resonators can depend on the chosen method of actuation. The most promising method of actuation at present appears to be piezoelectric actuation. Two methods of detection are considered, namely piezoresistive and piezoelectric detection. The mode can be a symmetric two dimensional plate mode expansion (with a corresponding compression of the thickness).

Surface Chemistry

Controlling the chemistry of the surfaces of the NEMS devices and the microfluidics channels can be important. For example, within microfluidics channels, the surface to volume ratios can be very large (e.g., 0.08 $\mu m^{-1}$ in the channels, compared with about $5 \times 10^{-4}$ $\mu m^{-1}$ in a T-25 tissue culture plate). As a result, proteins and cells can stick to the surfaces creating cell cultures in unwanted places and potentially depleting media of critical proteins. In one embodiment, to prevent nonspecific binding of proteins and cells, the channels can be treated with a solution of 1% Pluronics F127 in PBS. Pluronics are a class of nonionic tri-block copolymers composed of a central hydrophobic chain of polyoxypropylene (poly(propylene oxide)) flanked by two hydrophilic chains of polyoxyethylene (poly(ethylene oxide)). See e.g., BASF, *Pluronic® F127 Block Copolymer Surfactant, in Technical Bulletin.* 2002: Mount Olive. The hydrophobic polyoxypropylene can stick to the hydrophobic PDMS channels and the hydrophilic polyoxyethylene end groups can be presented into the channel and prevent nonspecific binding of cells and proteins.

Controlling the surfaces of the NEMS devices can be complex because there can generally be specific regions where the cells do attach and others where they do not attach. Thus, it can be important to control and standardize the interaction between the cell and the force sensor. In one embodiment, the regions where cells can attach can be made hydrophilic using a self-assembled monolayer (SAM), while the remaining hydrophobic regions can be passivated by, for example, treating the cell chamber with Pluronics, which can stick to the hydrophobic areas but not the hydrophilic areas.

In one embodiment, the microfluidics are bonded to the NEMS chips by a room temperature oxygen plasma. To render the surface, particularly one deposited after the oxygen plasma, hydrophobic, vapor deposition of a fluorinated silane monolayer can be used. Compositions that can be used for the vapor deposition can include (Tridecafluoro-1,1,2,2-tetra-hydrooctyl)Dimtheylchloro-silane, (Tridecafluoro-1,1,2,2-tetra-hydrooctyl)trichloro-silane, or a combination thereof.

A self assembled monolayer can be applied thereafter to the surface, which can comprise pads comprising noble metals, including gold, using thiol based chemistry. Polymer can be deposited by any conventional methods (e.g., spin deposition) on a wafer, which can comprise, for example, silicon, and gold pads can be patterned by any methods on top of the polymer surface. Any lithography method can be used, including photo lithography, direct write lithography, e-beam lithography, or combinations thereof. The gold surfaces can be further treated, for example, with titanium or MPTS to mimic the adhesion layer used in the NEMS fabrication process. The SAM can comprise a wide range of materials. For example, it can comprise carboxylic acid, hydroxyl groups, polyethylene-glycol (PEG), or combinations thereof. SAM can be deposited from either solvent (e.g., ethanol) or an aqueous solution. The SAM can comprise 11-mercapto-1-undecanoic acid, 11-mercapto-1-undecanol, (1-Mercapto-11-undecyl) tri(ethylene glycol), or combinations thereof. SAM can be deposited from ethanol solutions of aqueous solutions.

In one embodiment, certain regions of the polymer can then be coated with Pluronics F127 Prill (BASF). Additionally, the surface of the polymer can be further treated with Pluronics diluted in a phosphate buffer solution (PBS). Pluronics can stick to the hydrophobic surfaces and prevent cells and proteins from sticking. Meanwhile, it also can leave the surface hydrophilic.

Cell attachment to the hydrophilic regions can be further encouraged by treating the cell chamber with an additional composition, such as a fibronectin (FN) solution. Fibronectin is a high-molecular weight extracellular matrix (ECM) glycoprotein that can bind to trans-membrane integrins with a well characterized Arginine-Glycine-Aspartic Acid (RGD) sequence. Fibronectin can encourage and accelerate cell adhesion and spreading, and thus an option step of coating the region can be employed. Finally, the fibronectin will stick only to the hydrophilic areas because the Pluronics will block attachment elsewhere.

Monitoring Cell Response

The force sensor can be used to monitor the response of the cells when they are under a certain stimulus or perturbation. Any cells, such as eukaryotic cells can be used. The cells can be adherent cells, such as fibroblasts or endothelial cells. The cells can include NIH-3T3, CHO (Chinese Hampster Ovary cells), NIH-3T6, HELA, SV-80 human fibroblasts, HFF (Human foreskin fibroblasts), REF52 (Rat embryo fibroblasts), HEK 293 (Human Embryonic Kidney cells), L-929 (Mouse fibroblastic cells), B16-F1 (Mouse melanoma cells), CCL71 goldfish fin fibroblasts, PtK1 epithelial cells, MEF-hC3G, RBL-2H3 Rat basophilic leukemia.

The responses of the cells can include physiological changes occurring in the cells, such as structural change or conformation change. The response can also be a force response or a strain response (or a combination thereof) of the cells. For example, cells such as fibroblasts are generally known to able to exert force onto a substrate, and such force can cause strain in the substrate and/or the cell itself. The responses being monitored by the force censor need not be a response from a whole cell. For example, the responses can be those of the lamellipodium, microtubule, stress fiber, focal adhesion, cytoskeleton, or a combination thereof.

Any suitable reagent that can perturb the cell and trigger a response of the cell can be used. The reagent can be any chemical reagent, such as a pharmaceutical drug. The reagent can trigger different types of responses. For example, it can promote protein binding. Alternatively, it can inhibit protein binding. The response, as described previously, can come from any part of the cells. The reagent can be an actin perturbing reagent, which can be, for example, cytochalasin A, B, C, D, E, H, and J, latrunculin A and B, jasplakinolide, or combinations thereof. Cytochalasin D is a small molecule produced by a fungus (*Zygosporium mansonii*) that is a potent disruptor of cytoskeletal force. It can be a myosin perturbing reagent, such as blebbistatin, calyculin A, or a combination thereof. The reagent can also be a microtubule perturbing reagent, which can be, for example, paclitaxel (taxol), laulimalide, vinca alkaloids, colchicines, isopropyl N-3-chlorophenyl carbamate, or combinations thereof. The reagent can also be an integrin perturbing reagent, including Arginine-Glycine-Aspartic Acid (RGD), trypsin (Invitrogen), EDTA (Invitrogen), versene (Invitrogen), or combinations thereof. It can also be a rho-Rac perturbing reagent, including lysophosphatidic, rho-kinase, mDia, the cytotoxic-necrotixing factor produced by several pathogenic strains of *E. coli*, C3, an exotransferase produced by clostridium botulinum, Y-27632, N-WASP, or combinations thereof.

One response of the cells, when subject to a reagent, can be that the cell exerts a force on the force sensor beam. As a result, the force can exert a strain on the strain sensor (e.g., a piezoresistor) and/or the polymer layers. The lengthening of the wire in the strain sensor inside the beam can cause a change in electrical signal, which can be detected by the force sensor. The response of the cell to such reagent can then thereby be observed.

The cells need not be deposited onto the force sensor directly. For example, in one embodiment, the cells are disposed onto a movable member or platform, which is separate from the force sensor, but which is adjacent to the force sensor. At least one of these cells are allowed to stretch and touch the force sensor from the platform, and the force exerted by the cell can then be monitored by the force sensor by the methods described previously.

Phenotypic Screening

Figure 2:
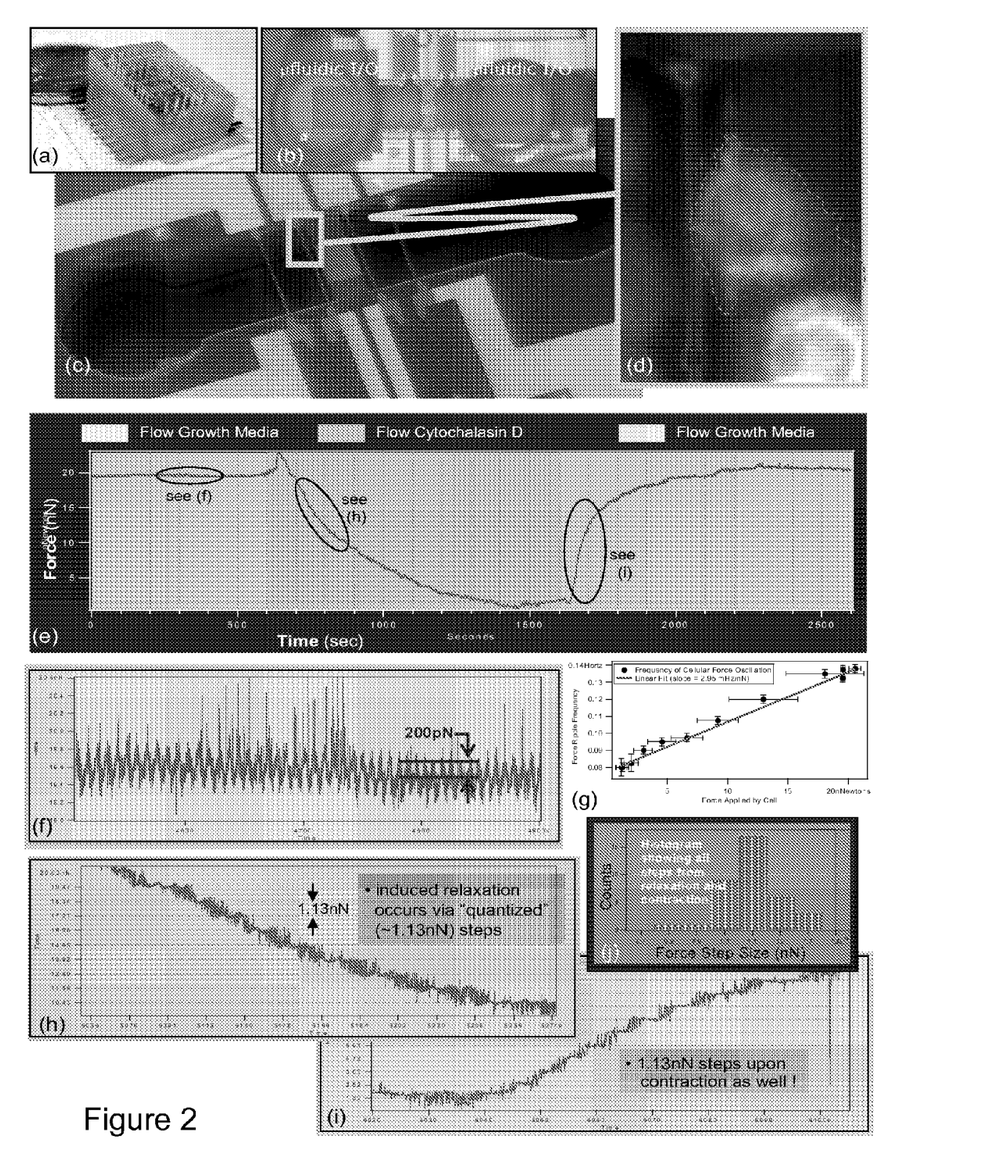

NEMS force sensors can be used in phenotypic screening. In one embodiment, the method can be described as follows: cells can be allowed to adhere to the force sensor and baseline measurement of cellular force can be obtained. Cells can then be exposed to one or more potential reagents, such as a pharmaceutical reagent, such as a drug, introduced in a carefully controlled manner using the integrated microfluidics, and the effects of the reagent(s) on the cells, such as the force exerted by the cells, is monitored. Since the cytoskeleton can couple to many aspects of a cell's physiology, the force thus can provide a broad but highly sensitive measure of affect by the reagent(s). Fluorescent microscopy can be integrated with the force sensor system described herein and be performed in parallel, as illustrated in FIG. 2. In one embodiment wherein fluorescent microscopy is used, a dye is introduced into the system (e.g., the cells) to allow for detection.

Figure 1:
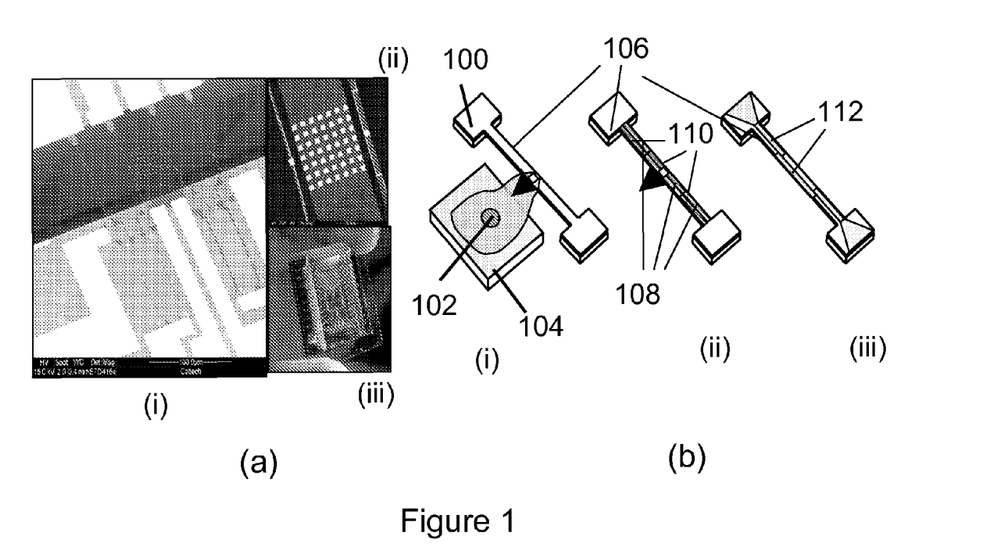
FIG. 1a provides electron micrographs of suspended beams (FIG. 1a(i)), a zoom-in image thereof (FIG. 1a(ii)), and an optical image of microfluidics encapsulated chip held between thumb and forefinger (FIG. 1a(iii)).
FIG. 1B provides schematics showing a cell attaching and spreading on the large center gold pad then reaching the force sensors on both sides (FIG. 1b(i)), causing lengthening of the wires.

The reagent can cause the cell to change in its physiology, such as conformation and/or structure, or change its force response to the reagent. The perturbation can cause the cytoskeleton of the cell to react. When the cell exerts a force onto the force sensor, the strain sensor, including the metal wire, can lengthen along the length of the wire, while narrowing along the width of the wire (with substantially constant volume). Such response of the cell can be found in, for example, FIG. 1a-1b. As shown in FIG. 1b(i), the cell 102 is deposited onto the platform 104 adjacent to the NEMS 100. After the cell is exposed to a reagent, the cell 102 stretches and provides a force on the clamped beam 106 of the NEMS 100. The beam 106 can bend or deform in the direction of the arrow, which can cause beam regions 108 to lengthen and regions 110 to shorten. As shown in FIG. 1b(ii), since the metal wire 112 is located in the middle of beam 106 under regions 108, the entire wire 112 (FIG. 1b(ii)) is lengthened and narrowed by the force of the cell. The lengthening of the wire can then be detected.

One advantage of NEMS force sensors for phenotypic screening can be the high sensitivity to perturbations of the cellular cytoskeleton. NEMS force sensors can be sensitive to subtle effects of potential reagents that other screening methods will miss—this can allow for detection of subtle activity that is desired in potential pharmaceuticals. Additionally, NEMS force sensors can be compatible with microfluidic systems, thereby reducing the quantity of reagent, and thus cost, needed for a screening test. Microfluidic compatibility also can enable a degree of system automation and parallelization desirable for high throughput screening. Large arrays of NEMS force sensors can be fabricated and integrated for high throughput screening. Moreover, NEMS force sensors can be integrated with fluorescent microscopy. This enables molecular level monitoring of activity within a cell, a second method of monitoring cellular physiology and a very common tool used in high-content pharmaceutical screening, see (Abraham et al., *Trends Biotechnology* 22 (2004), 15-22; Korn et al., *Current Opinion in Chemical Biology* 11 (2007), 503-510).

NON-LIMITING WORKING EXAMPLES

Example 1

Surface Chemistry

A force sensor comprising a polymer surface with gold pads was used. The cells were to be attached to the pads and not to the polymer. At the beginning, both the pad and the polymer surfaces were hydrophobic, and water contact angle was about 80° on both.

A self assembled monolayer was applied to the gold pads using thiol based chemistry. The SAM used were 11-mercapto-1-undecanoic acid, 11-mercapto-1-undecanol, (1-Mercapto-11-undecyl) tri(ethylene glycol). Monolayers were deposited from ethanol solutions of aqueous solutions. The monolayers left the gold surface hydrophilic, and water contact angle was about 25°.

The polymer regions were coated with Pluronics F127 Prill (BASF). The surfaces were treated to Pluronics diluted in PBS (phosphate buffer solution), 0.02% to 1% by weight for 20-80 min. Pluronics was found to stick to the hydrophobic polymer surfaces and prevented cells and proteins from sticking. Pluronics left the surface hydrophilic.

The gold regions were coated with Fibronectin. The surfaces were treated with fibronectin diluted in PBS, 5 ug/mL to 50 ug/mL for 20 min-4 hrs. Fibronectin was found to stick to the self assembled monolayer on the gold surface, but not to Pluronics on polymer surface.

Figure 3:
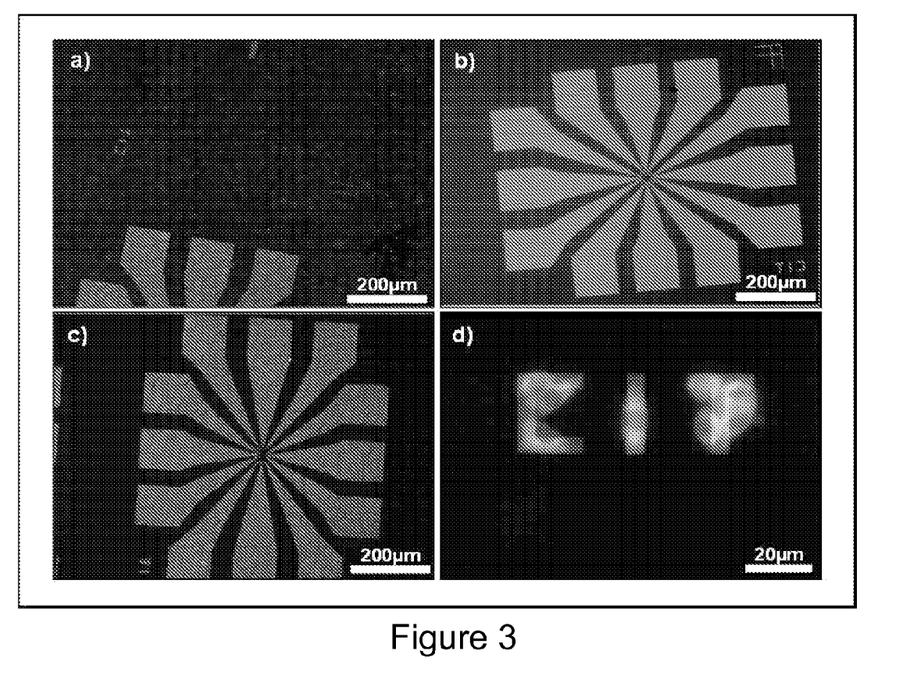
FIG. 3a shows results of a typical fibronectin only test: cells are spread everywhere.
FIG. 3b is from a Pluronics only test: almost no cells present and none are spread.
FIG. 3c-3d show results from complete surface chemistry process (SAM, Pluronics and fibronectin): cells are well spread on the gold and absent from the polymer

The results are shown in FIG. 3. The surface with only fibronectin (FIG. 3(a)), cells were spread everywhere. Almost no cells were present and none was spread on a surface with only Pluronics (FIG. 3(b)). FIGS. 3(c) and 3(d) show results from complete surface chemistry process (SAM, Pluronics and fibronectin), wherein cells were well spread on the gold and absent from the polymer. Thus, modifying surface chemistry allowed control of the cell adherence and/or spreading.

Example 2

Monitoring Cell Response

FIGS. 2a-2j demonstrate the results of screening the force response of individual fibroblasts (NIG-3T3) to perturbing agent cytochalasin D, as detected by the polymer NEMS force sensors.

The lamellipodia of the fibroblasts responded to the perturbation by the cytochalasin, but were allowed to recover in growth media (FIG. 2b). The temporal force response of the lamellipodia was recorded and shown in FIG. 2e. Small force oscillations roughly 400 pN peak-to-peak, with a frequency that is monotonically dependent on the force being exerted by the lamellipodia were observed (FIGS. 2f-2h). FIG. 2g illustrating the linearity of frequency dependence. FIGS. 2h-2i show that large, stable, quantized force steps of order 1 nN are manifested when a cell's cytoskeleton is perturbed with cytochalasin D and allowed to recover in growth media. A histogram of the step sizes is presented in FIG. 2j.

The foregoing description of the embodiments of the invention has been presented for purposes of illustration and description. It is not intended to be exhaustive or to limit the invention to the precise form disclosed, and modifications and variations are possible in light of the above teaching or may be acquired from practice of the invention. The embodiments were chosen and described in order to explain the principles of the invention and as a practical application to enable one skilled in the art to utilize the invention in various embodiments and with various modification are suited to the particular use contemplated. It is intended that the scope of the invention be defined by the claims appended hereto and their equivalents.

What is claimed:

1. A method of screening one or more cells, comprising:
providing one or more cells to a nanoelectromechanical system (NEMS) force sensor that is encapsulated by a microfluidics channel that controls a fluidic environment around the force sensor, wherein the NEMS force sensor comprises a doubly clamped beam that is integrated with a strain sensor, and wherein the strain sensor converts a deformation of the doubly clamped beam into an electrical signal;
applying at least one reagent to the one or more cells; and
measuring a change in the electrical signal of the strain sensor caused by a lengthening of the strain sensor, thereby observing a response of the one or more cells to the reagent with the NEMS force sensor and screening the one or more cells.

2. The method of claim 1, further comprising establishing a baseline measurement of the response of the one more or cells on the force sensor.

3. The method of claim 1, further comprising measuring effects of the reagent on force exerted by the one more or cells.

4. The method of claim 3, wherein one of the effects comprises changes in cell physiology.

5. The method of claim 3, wherein one of the effects comprises changes in cell structure.

6. The method of claim 3, wherein one of the effects comprises changes in cell conformation.

7. The method of claim 1, wherein the reagent causes at least one perturbation in cytoskeleton of the one or more cells.

8. The method of claim 1, further comprising observing the one or more cells by fluorescent microscopy.

9. The method of claim 1, wherein the observance of the response of the one or more cells to the reagent is further performed by phenotypically screening the one or more cells.

10. The method of claim 1, wherein the force sensor comprises SU8, parylene, polyimide, or combinations thereof.

11. The method of claim 1, wherein the force sensor further comprises at least one metal wire, which wire is configured such that the force sensor lengthens along the length of the wire and narrows along the width of the wire when the one or more cell responds to the reagent.

12. The method of claim 1, wherein:
the strain sensor comprises a piezoresistive strain sensor that is patterned asymmetrically in a horizontal plane of the doubly clamped beam to measure in-plane responses.

13. The force sensor of claim 1, wherein:
the strain sensor comprises a piezoresistive strain sensor that is patterned asymmetrically in a vertical plane of the doubly clamped beam to measure out-of-plane responses.

14. The method of claim 1, wherein the force sensor comprises at least one metal wire comprising a noble metal.

15. The method of claim 1, wherein the force sensor is fabricated on a silicon-nitride coated silicon wafer and suspended over an opening etched in the wafer.

16. The method of claim 1, wherein the reagent comprises a cytochalasin.

17. A method of evaluating effects of a drug reagent, comprising:
providing one or more cells to a nanoelectromechanical system (NEMS) force sensor that is encapsulated by a microfluidics channel that controls a fluidic environment around the force sensor, wherein the NEMS force sensor comprises a doubly clamped beam that is integrated with a strain sensor, and wherein the strain sensor converts a deformation of the doubly clamped beam into an electrical signal;
applying the drug reagent to the one or more cells; and
measuring a change in the electrical signal of the strain sensor caused by a lengthening of the strain sensor, thereby observing a response of the one or more cells to the drug reagent with the NEMS force sensor.

18. The method of claim 17, wherein the cells are adhesion cells.

19. The method of claim 17, wherein the drug reagent inhibits protein binding.

20. The method of claim 17, wherein the drug reagent promotes protein binding.

21. A method of screening one or more cells, comprising:
providing one or more cells;
providing a nanoelectromechiancal system (NEMS) force sensor that is encapsulated by a microfluidics channel that controls a fluidic environment around the force sensor, wherein the NEMS force sensor comprises a doubly clamped beam that is integrated with a strain sensor, and wherein the strain sensor converts a deformation of the doubly clamped beam into an electrical signal;
disposing the one or more cells to a platform which is separate from but adjacent to the NEMS force sensor;
applying at least one reagent to the one or more cells; and
measuring a change in the electrical signal of the strain sensor caused by a lengthening of the strain sensor, thereby observing a response of the one or more cells to the reagent and effect of the response upon the NEMS force sensor and screening the one or more cells.

22. The method of claim 21, wherein the force sensor is part of an array of NEMS force sensors and the response comprises a force exerted by one or more cells on the force sensor.

* * * * *